United States Patent
Matthiessen et al.

(10) Patent No.: US 7,288,943 B2
(45) Date of Patent: Oct. 30, 2007

(54) ELECTROIMPEDANCE TOMOGRAPH WITH COMMON-MODE SIGNAL SUPPRESSION

(75) Inventors: Hans Matthiessen, Bad Schwartau (DE); Dieter Weismann, Gross Grönau (DE); Jianhua Li, Lübeck (DE); Yvo Gärber, Lübeck (DE)

(73) Assignee: Dräger Medical AG & Co. KG (DE)

( * ) Notice: Subject to any disclaimer, the term of this patent is extended or adjusted under 35 U.S.C. 154(b) by 0 days.

(21) Appl. No.: 11/419,318

(22) Filed: May 19, 2006

(65) Prior Publication Data
US 2007/0007973 A1   Jan. 11, 2007

(30) Foreign Application Priority Data
Jul. 7, 2005   (DE)   ............... 10 2005 031 751

(51) Int. Cl.
G01R 27/04 (2006.01)
G01R 27/08 (2006.01)
A61B 5/04 (2006.01)
A61B 5/05 (2006.01)

(52) U.S. Cl. ............ 324/628; 324/692; 600/546; 600/547

(58) Field of Classification Search ............ 324/628, 324/692
See application file for complete search history.

(56) References Cited

U.S. PATENT DOCUMENTS 5,810,742 A * 9/1998 Pearlman .......... 600/547
6,280,395 B1 * 8/2001 Appel et al. .......... 600/546
2003/0073916 A1 * 4/2003 Yonce .......... 600/509
2006/0264775 A1 * 11/2006 Mills et al. .......... 600/547

* cited by examiner

Primary Examiner—Anjan Deb
Assistant Examiner—Jeff Natalini
(74) Attorney, Agent, or Firm—McGlew and Tuttle, P.C.

(57) ABSTRACT

An electroimpedance tomograph is provided with a plurality of electrodes (1), which can be placed on the body of a patient and are connected to a control and evaluating unit (20) via a selector switch (60). The control and evaluating unit (20) cooperates with the selector switch (60) such that two electrodes each are supplied with alternating current from an AC power source (22). The detected analog voltage signals of the other electrodes are sent into the control and evaluating unit (20) via a measuring amplifier (62) and AD converter (64) and are processed there in order to reconstruct the impedance distribution of the body in the plane of the electrodes therefrom. A symmetrical AC power source (22) is used to reduce common-mode signals. To make it possible to suppress errors due to common-mode signals, provisions are made for the control and evaluating unit (20) to be set up for making available an additional common-mode signal at an output during an adjusting mode of operation and to send it to the body via common-mode signal electrodes (4, 90) that can be placed on the body. The control and evaluating unit (20) is prepared, furthermore, to adjust the measuring amplifier (62) according to value and phase for each electrode pair connected by the selector switch (60) such that the common-mode signal at the output of the measuring amplifier (62) is minimized, and the adjusted parameters are stored for each electrode pair.

15 Claims, 2 Drawing Sheets

ELECTROIMPEDANCE TOMOGRAPH WITH COMMON-MODE SIGNAL SUPPRESSION

CROSS REFERENCE TO RELATED APPLICATIONS

This application claims the benefit of priority under 35 U.S.C. § 119 of German Patent Application DE 10 2005 031 751.0 filed Jul. 7, 2005, the entire contents of which are incorporated herein by reference.

FIELD OF THE INVENTION

The present invention pertains to an electroimpedance tomograph with a plurality of electrodes, which can be arranged on the body of a patient and which are connected via a selector switch to a control and evaluating unit, wherein the control and evaluating unit cooperates with the selector switch such that two electrodes each are supplied with alternating current from an AC power source and the detected analog voltage signals of the other electrodes are sent into the control and evaluating unit via a measuring amplifier and are processed there in order to reconstruct from this the impedance distribution of the body in the plane of the electrodes, a symmetrical AC power source being used to reduce common-mode signals.

BACKGROUND OF THE INVENTION

A measuring technical problem in electroimpedance tomography is that the useful signal used to calculate the graphic representation must be sufficiently larger than the particular interferences. The simple increase in the measuring current has limits, because the currents that are permissible according to the standards are limited (in a frequency-dependent manner). Consequently, it is necessary to reduce the interference signals. Moreover, the interference signals consist partly of self-generated interferences, e.g., the crosstalk or the so-called common-mode signal, which increase proportionally to the increase in the current. Increasing the measuring current can improve the distance from the external interferences at best.

Electrical impedance tomography (EIT) is a method for reconstituting impedance distributions or, in case of functional EIT for reconstituting impedance changes relative to a reference distribution, in electrically conductive bodies. A plurality of electrodes are arranged for this purpose on the conductive surface of the body being examined, and the control unit, usually a digital signal processor, ensures that a pair of (preferably) adjacent electrodes each is supplied consecutively with an electric alternating current (for example, 5 mA at 50 kHz), and the electric voltages are detected at the remaining electrodes acting as measuring electrodes and are sent to the control unit. The impedance distribution or, in case of functional electroimpedance tomography, the change in that impedance distribution relative to a reference distribution can be reconstructed with suitable algorithms by the combination of the measured voltage values during the consecutive rotating current feeds. A ring-shaped, equidistant array of 16 electrodes is used in typical cases, and these electrodes can be placed around the body of a patient, for example, with a belt. Alternating current is fed into two adjacent electrodes each, and the voltages are measured between the remaining currentless electrode pairs acting as measuring electrodes and recorded by the control unit. By rotating the current feed points, a plurality of measured voltage values are obtained, from which a two-dimensional tomogram of the impedance distribution can be reconstructed relative to a reference in the plane of the electrode.

Such tomograms are of interest in medicine because the impedances depend on the biological state of the organs (for example, the breathing state of the lungs) and/or the frequency of the current. Therefore, both measurements at different states are performed at a given feed frequency and in different biological states (for example, observation of the breathing cycles) and measurements at different frequencies performed at different feed frequencies and identical biological state in order to obtain information on the corresponding impedance changes. As was already mentioned, functional impedance tomography of the lungs, in which the electrodes of the EIT device are arranged around the patient's thorax, is an important application. One of the interferences occurring in terms of measuring technique during impedance tomography is the ultimately unavoidably occurring residual asymmetry of the alternating current feed on the body, which also occurs when a symmetrical AC power source is used, which is due to the differences in the routing of the cables to the different electrodes, different contact resistances, etc.

The power source supplies an alternating current alternating between 20 kHz and several MHZ for the measurement. To evaluate the causes of the development of the asymmetry of current feed, it is consequently necessary to use not only disturbing differences in the ohmic resistors but also those in the AC impedances. The use of alternating current is necessary for medical reasons. The permissible measuring currents would be even lower by several orders of magnitude in case of direct current. Moreover, the measurement with alternating current makes possible a low-drift, frequency-selective demodulation of the measuring currents and to obtain information on how the impedances of the upper body change with the frequency.

FIG. 3 shows a basic circuit diagram of an electroimpedance tomograph of the type mentioned in the introduction, which embodies a symmetrical AC power source due to the insertion of a power source 22 or an isolation transformer 40 between the AC power source 22 and the selector switch (multiplexer) 60. The primary circuit of this isolation transformer 40 has clear references and consequently usually asymmetries to the ground (the measuring technical reference point of the device) due to the circuitry. To keep the effect of the asymmetry on the secondary side as limited as possible via stray capacitances, a shield winding, which is grounded, is located between the two windings. If no asymmetrical stray capacitances of the secondary side are desired against this shield winding, the secondary winding must have a symmetrical design in relation to the shield winding. This symmetrical design has, of course, limits, so that the stray capacitances must be assumed to be different on both sides of the secondary winding in relation to the ground in an equivalent circuit. This is only one example of how extensive symmetry of the alternating current feeds is sought to be achieved.

FIG. 4 shows an equivalent circuit to explain the asymmetries of the AC signal applied in the device from FIG. 3. Asymmetries in the power source are only part of the asymmetries occurring in the measuring circuit. Other causes are the multiplexer or selector switch 60, which has different conducting-state DC resistances $R_{ML}$ and $R_{MR}$ for the two terminals (depending on the channel being used) and also different stray capacitances $C_{ML}$ and $C_{MR}$ in relation to the electric environment. The multiplexer 60 is followed by the shielded connecting line, so that the capacitive differences in $C_{LR}$ and $C_{LL}$ against the ground of the two connecting lines to the electrodes are to be taken into account. The inductive and resistive line impedances $Z_{LL}$ and $Z_{LR}$ are other sources of asymmetry especially in case of differences in the lengths of the connecting lines and at high measuring current frequencies.

Finally, the transition impedances of the electrodes against the skin surface are finite and different, which is likewise to be taken into account. Moreover, they are complex, i.e., they are composed mainly of the transition resistances $R_{EL}$ and $R_{ER}$ and the transition capacitances $C_{EL}$ and $C_{ER}$.

All asymmetries combined produce the result that there are different flows of measuring currents from the two lines via the stray capacitances against the ground and different voltage drops at the longitudinal impedances and consequently there are differences in current flow between the two feed terminals, because more or less different current components will have now flown to the ground before and the differential current flows to the ground via the body resistance and the transition impedance of the reference ground electrode and thus it generates a common-mode signal on the body and consequently on the measuring electrodes. This common-mode signal is different for all actuated electrode positions both because of the differences in the channels of the multiplexer 60 as well as the external lines and of the electrode transition resistances and generates at the measuring amplifier error signals, which may overlap the useful signals, together with the value and the differences of the transition impedances of the particular measuring electrodes (which are connected by the multiplexer 60) with the finite common-mode reduction resulting therefrom.

Even if the measuring amplifier behind the multiplexer were ideal, the electrodes of the particular connected measuring lines would again generate asymmetries and only a finite common-mode signal suppression in a manner that is the reverse of what happens in case of the current path via the parasitic impedances and the values thereof, which differ from one measuring channel to the next.

One possibility of keeping this common-mode signal as low as possible is a reference ground electrode with a very low transition impedance. The size of the possible reference ground electrodes and their ability to be handled are limited and, beginning from a certain size, they generate movement artifacts, which originate from the changes in the transition impedance that are generated during the movement of the patient. Therefore, this measure has only limited effectiveness.

SUMMARY OF THE INVENTION

The object of the present invention is therefore to provide an electroimpedance tomograph in which interferences with the measured signals due to common-mode signals are further suppressed.

According to the invention, an electroimpedance tomograph is provided with a plurality of electrodes, which can be placed on the body of a patient and are connected to a control and evaluating unit via a selector switch. The control and evaluating unit cooperates with the selector switch such that two electrodes are each supplied with an alternating current from an AC power source and the detected analog voltage signals of the other electrodes are sent into the control and evaluating unit via a measuring amplifier and a AD converter and are processed there in order to reconstruct therefrom the impedance distribution of the body in the plane of the electrodes. A symmetrical AC power source is used to reduce common-mode signals. The control and evaluating unit is set up to make available an additional common-mode signal at an output during an adjusting mode of operation and to send the additional common-mode signal to the body via common-mode signal electrodes that can be placed on the body. The control and evaluating unit is set up, furthermore, to adjust the measuring amplifier according to value and phase for each electrode pair connected by the selector switch such that the common-mode signal at the output of the measuring amplifier is minimized. Adjusted parameters are stored for each electrode pair. The control and evaluating unit is furthermore set up to poll the corresponding adjusted parameters during the measuring mode for each connected electrode pair and to adjust the measuring amplifier according to these parameters.

Consequently, this device is able to purposefully apply an additional common-mode signal to the body via common-mode signal electrodes. This common-mode signal, applied in a purposeful manner, propagates into the measuring amplifier for each electrode pair that is switched through. The control and evaluating unit is thus set up, e.g., by programming and adjusting circuits, which are controllable as a result, at the measuring amplifier to adjust the measuring amplifier such that the common-mode signal, which is applied to the body and which also appears in the measuring amplifier via the particular electrode pair and the selector switch, is minimized at the output of the measuring amplifier. After this adjustment, the measuring amplifier can also be adjusted during an EIT measurement with the adjusted parameters stored for each electrode pair, and it will output, as a result, common-mode signals appearing during the measurement only minimally at its output.

The additional common-mode signal is preferably applied by means of an analog control loop circuit. The analog control loop circuit has a differential amplifier, one input of which is connected to the output of a common-mode signal electrode that can be placed on the patient's body and whose other input is connected to the output for the common-mode signal generated additionally. The output of the differential amplifier is connected to a common-mode signal electrode, which can be placed on the body. The control and evaluating unit is set up to ground the output for the additional common-mode signal in the measuring mode. As a result, a control circuit with active grounded electrode (the common-mode signal electrode connected to the output of the differential amplifier) is embodied in the measuring mode.

It is preferred if the control and evaluating unit is set up for making available the additional common-mode signal with the same frequency as that of the symmetrical AC power source, so that the common-mode signal generated additionally for the purposes of adjusting has the same frequency as common-mode signals appearing during the measuring mode.

The adjustment of the measuring amplifier can be made possible, e.g., by one branch of the measuring amplifier being connected, on the one hand, to the ground via an ohmic resistor and a transistor and, on the other hand, to the group via a capacitor and a transistor. The control and evaluating unit drives the transistors via a digital-analog converter in order to control the coupling of the ohmic resistor and of the capacitor, in order to achieve suppression of the common-mode signal according to value and phase as a result.

The present invention will be described below on the basis of exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
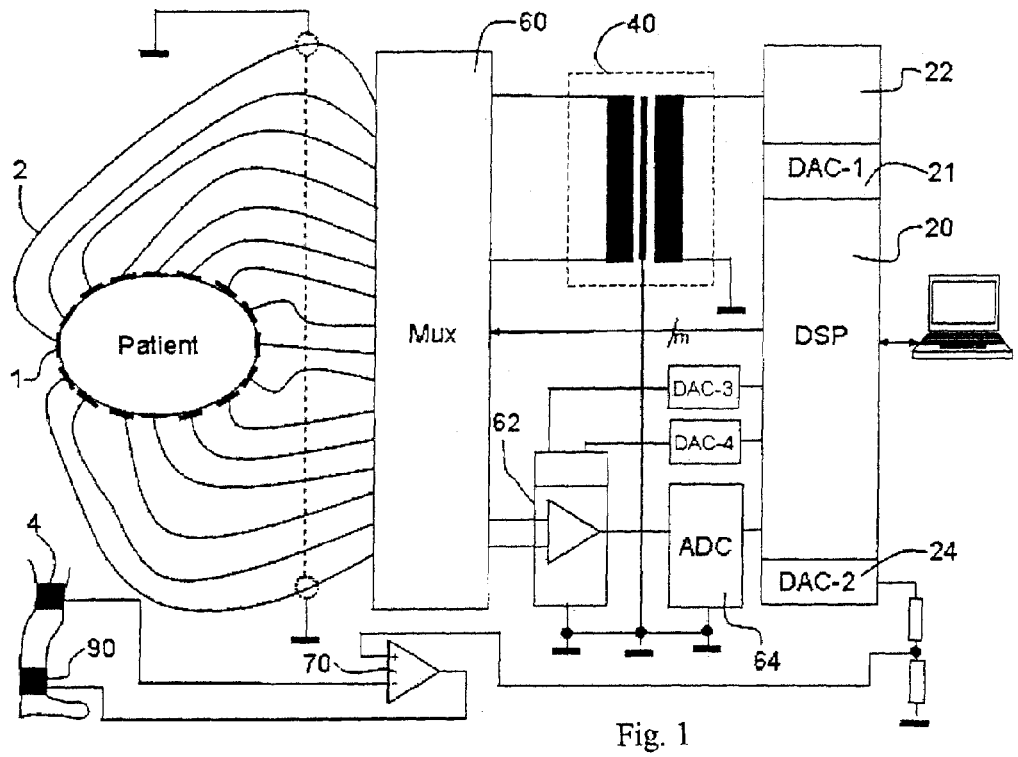
FIG. 1 is a block diagram of an embodiment of an electroimpedance tomograph.

Referring to the drawings in particular, the electroimpedance tomograph shown in FIG. 1 has a control and evaluating unit 20, which is connected via a digital-analog converter 21 to an AC power source 22 for controlling same. The alternating current of the power source 22 is galvanically separated from the selector switch 60 via an isolation transformer or transformer 40. The selector switch or multiplexer 60 applies the AC signal with the cable 2 to two electrodes 1 each (only one of a total of 16 electrodes is provided with a reference number). The other electrodes are then used consecutively as measuring electrodes in pairs. The voltage signals of the measuring electrodes are sent to the control and evaluating unit 20 via the multiplexer 60 and a differential amplifier 62 and an analog-digital converter 64. The feeding electrode pairs 1 rotate now around the patient's body, controlled by the control and evaluating unit 20 and the multiplexer 60, and an electroimpedance tomogram is generated from this sequence in the control and evaluating unit 20.

Figure 2:
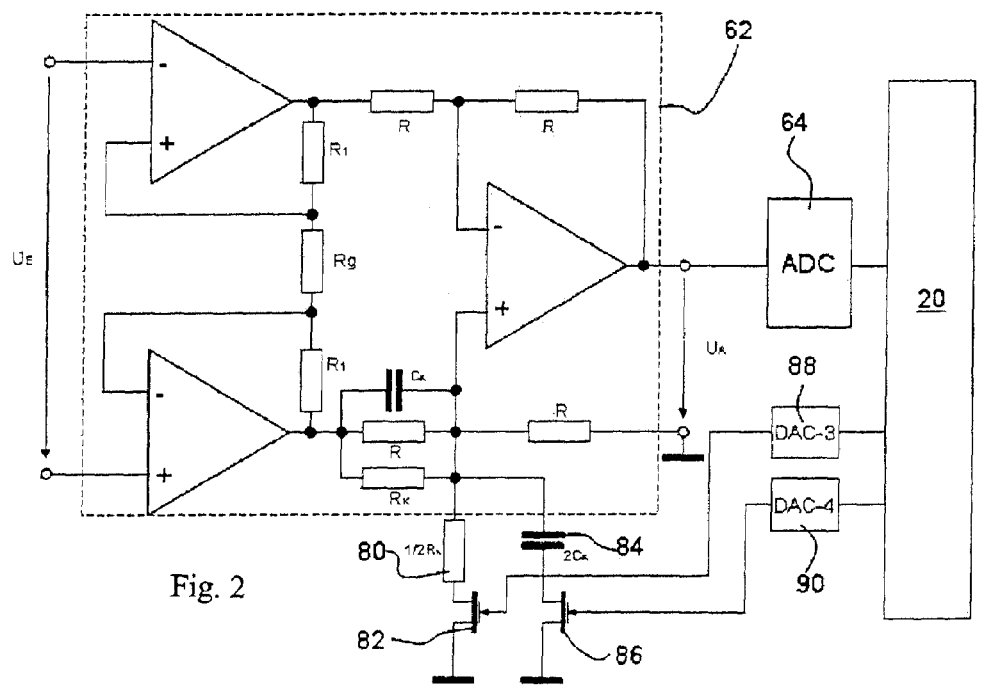
FIG. 2 is a block diagram of the measuring amplifier from the electroimpedance tomograph shown in FIG. 1.
Figure 3:
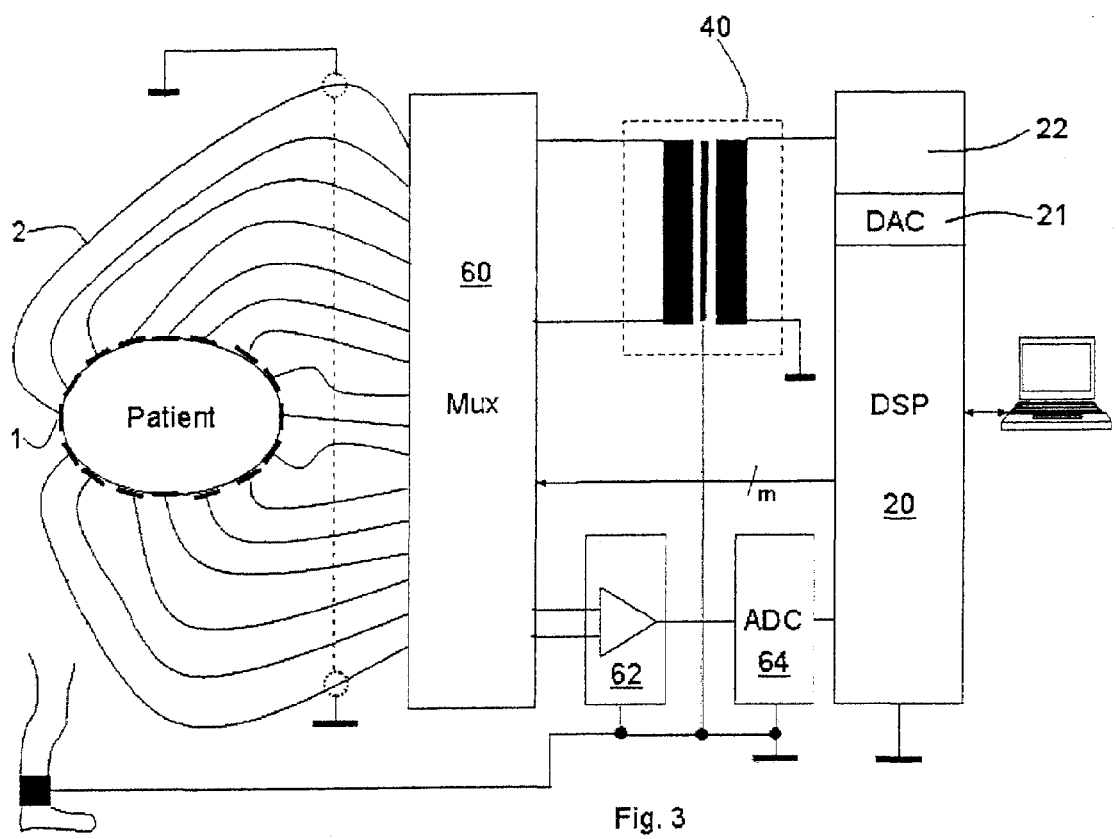
FIG. 3 is a block diagram of an electroimpedance tomograph according to the state of the art.
Figure 4:
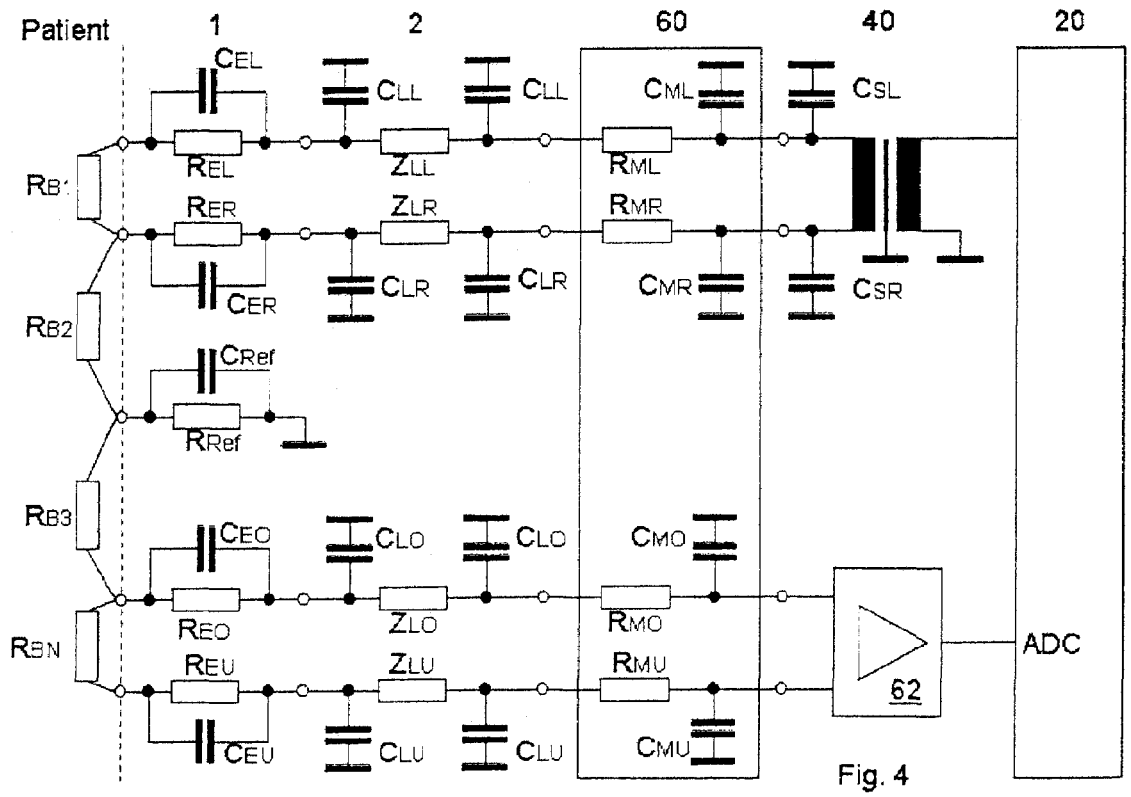
FIG. 4 is an equivalent diagram to explain the asymmetry occurring in the device shown in FIG. 3.

In the EIT device shown in FIG. 1, the control and evaluating unit 20 is provided, furthermore, with a digital-analog converter 24, via which a common-mode signal, preferably with the same frequency as that of the AC power source 22, is sent to a voltage divider. The output of the voltage divider with the additional common-mode signal is connected to one of the two inputs of a differential amplifier 70 of a control loop circuit. The other input of the differential amplifier 70 is connected to a common-mode signal electrode 4, which can be placed on the patient's body. The output of the differential amplifier 70 is connected to another active common-mode signal electrode 90, which can be placed on the body. A common-mode signal corresponding to the additional common-mode signal is generated on the body in this manner by the analog control circuit with the differential amplifier 70, This common-mode signal also propagates via the electrodes 1 and the selector switch 60 to the measuring amplifier 62. This measuring amplifier 62 is shown in greater detail in FIG. 2.

The control and evaluating unit 20 is set up, furthermore, to adjust the measuring amplifier 62, so that the common-mode signal at its output is minimized. Provisions are made for this purpose in the exemplary embodiment according to FIG. 2 for a branch of the measuring amplifier 62 to be connected, on the one hand, to the ground via an ohmic resistor and a control transistor 82 and, on the other hand, to the ground via a capacitor 84 and a control transistor 86.

These transistors 82, 86 are driven via the digital-analog converters 88, 90 by the control and evaluating unit. It is thus possible that the control and evaluating unit 20 varies the conductivity of the transistors 82 and 86 with an adjusting algorithm programmed in it and performs this variation until a minimum common-mode signal is left at the output of the measuring amplifier 72 via the analog-digital converter 64. It is thus possible to apply a common-mode signal generated extra to the body during an adjusting phase of the EIT device, and this common-mode signal will then travel the same route through the electronic unit into the measuring amplifier as will the measured signal proper during the later, actual measuring mode. When the differential amplifier 70 is now adjusted during the adjusting phase for each electrode pair such that the "artificial" additional common-mode signal at its output is minimized, and the adjusted parameters are stored, the common-mode signals appearing during the measuring mode will also be minimized by the adjustment of the differential amplifier 70 with the respective adjusted parameters.

While specific embodiments of the invention have been shown and described in detail to illustrate the application of the principles of the invention, it will be understood that the invention may be embodied otherwise without departing from such principles.

What is claimed is:

1. An electroimpedance tomograph comprising:
a plurality of electrodes for placement on a body of a patient;
a control and evaluating unit;
a selector switch;
a measuring amplifier;
an AD converter;
a symmetrical AC power source, said electrodes being connected to said control and evaluating unit via said selector switch, wherein said control and evaluating unit cooperates with said selector switch such that two of said electrodes as an electrode pair are each supplied with an alternating current from said AC power source and the detected analog voltage signals of the other said electrodes are sent into said control and evaluating unit via said measuring amplifier and said AD converter and are processed there in order to reconstruct therefrom an impedance distribution of the body in the plane of said electrodes; and
common-mode signal electrodes for placement on the body of a patient, said symmetrical AC power source being used to reduce common-mode signals, said control and evaluating unit being set up to make available an additional common-mode signal at an output during an adjusting mode of operation and to send said additional common-mode signal to the body via said common-mode signal electrodes, and said control and evaluating unit furthermore being set up to adjust said measuring amplifier according to value and phase for each electrode pair connected by said selector switch such that the common-mode signal at the output of said measuring amplifier is minimized, and the adjusted parameters are stored for each electrode pair, wherein said control and evaluating unit is set up, furthermore, to poll the corresponding adjusted parameters during the measuring mode for each connected electrode pair and to adjust said measuring amplifier according to said adjusted parameters.

2. An electroimpedance tomograph in accordance with claim 1, further comprising:

an analog control loop circuit with a differential amplifier having an input connected to the output of one of said common-mode signal electrodes and having another input connected to the output for the common-mode signal generated additionally, and that the output of said differential amplifier is connected to another said common-mode signal electrodes, wherein the control and evaluating unit is set up to ground the output for the additional common-mode signal.

3. An electroimpedance tomograph in accordance with claim 1, wherein said control and evaluating unit is set up to make available said additional common-mode signal with a same frequency as that of said symmetrical AC power source.

4. An electroimpedance tomograph in accordance with claim 1, further comprising:
compensating members with at least one ohmic resistor, with at least one capacitor and with at least one said transistor, said compensating members being connected in one of the branches of said measuring amplifier to adjust said measuring amplifier, wherein said, at least one transistor can be driven by said control and evaluating unit via digital-analog converters in order to make it possible to minimize a common-mode signal present at said measuring amplifier at the output of said measuring amplifier by adjusting according to value and phase.

5. An electroimpedance tomograph in accordance with claim 4, wherein a first compensating member is coupled with the ground with said ohmic resistor and with said transistor and a second compensating member is coupled with the ground with said capacitor and with another transistor, wherein said transistors can be driven by said control and evaluating unit via said digital-analog converters.

6. An electroimpedance tomograph system comprising:
a plurality of electrodes placed on a body of a patient to provide electrode pairs;
a selector switch;
a measuring amplifier;
an AD converter;
a symmetrical AC power source;
common-mode signal electrodes placed on the body of the patient; and
control and evaluation means, said electrodes being connected to said control and evaluating means via said selector switch, said control and evaluating means cooperating with said selector switch for selectively supplying electrode pairs with an alternating current from said AC power source and for detecting analog voltage signals, of the other said electrodes, sent into said control and evaluating means via said measuring amplifier and said AD converter and for processing converted signals to reconstruct therefrom an impedance distribution of the body in the plane of said electrodes, said symmetrical AC power source being used to reduce common-mode signals, said control and evaluating means for making available an additional common-mode signal at an output during an adjusting mode of operation and to send said additional common-mode signal to the body via said common-mode signal electrodes, and said control and evaluating means for adjusting said measuring amplifier according to value and phase for each electrode pair connected by said selector switch such that the common-mode signal at the output of said measuring amplifier is minimized, and for storing the adjusted parameters for each electrode pair, and said control and evaluating means for polling the corresponding adjusted parameters during a measuring mode for each connected electrode pair and for adjusting said measuring amplifier according to said adjusted parameters.

7. An electroimpedance tomograph system in accordance with claim 6, further comprising:
an analog control loop circuit with a differential amplifier having an input connected to the output of one of said common-mode signal electrodes and having another input connected to the output for the common-mode signal generated additionally, and that the output of said differential amplifier is connected to another said common-mode signal electrodes, wherein the control and evaluating means is set up to ground the output for the additional common-mode signal.

8. An electroimpedance tomograph system in accordance with claim 6, wherein said control and evaluating means is set up to make available said additional common-mode signal with a same frequency as that of said symmetrical AC power source.

9. An electroimpedance tomograph in accordance with claim 6, further comprising:
compensating members with at least one ohmic resistor, with at least one capacitor and with at least one said transistor, said compensating members being connected in one of the branches of said measuring amplifier to adjust said measuring amplifier, wherein said, at least one transistor can be driven by said control and evaluating means via digital-analog converters in order to make it possible to minimize a common-mode signal present at said measuring amplifier at the output of said measuring amplifier by adjusting according to value and phase.

10. An electroimpedance tomograph system in accordance with claim 9, wherein a first compensating member is coupled with the ground with said ohmic resistor and with said transistor and a second compensating member is coupled with the ground with said capacitor and with another transistor, wherein said transistors can be driven by said control and evaluating means via said digital-analog converters.

11. An electroimpedance tomograph method comprising the steps of:
providing a plurality of electrodes placed on a body of a patient to provide electrode pairs;
providing a selector switch;
providing a measuring amplifier;
providing an AD converter;
providing a symmetrical AC power source;
providing common-mode signal electrodes placed on the body of the patient;
providing a control and evaluation unit;
connecting said electrodes to said control and evaluating unit via said selector switch;
using said control and evaluating unit in cooperation with said selector switch for selectively supplying electrode pairs with an alternating current from said AC power source and for detecting analog voltage signals of the other said electrodes sent into said control and evaluating unit via said measuring amplifier and said AD converter;
processing converted signals to reconstruct therefrom an impedance distribution of the body in the plane of said electrodes;
making available a common-mode signal at an output during an adjusting mode of operation;

sending said common-mode signal to the body via said common-mode signal electrodes, and said control and evaluating unit for adjusting said measuring amplifier according to value and phase for each electrode pair connected by said selector switch such that the common-mode signal at the output of said measuring amplifier is minimized;

storing the adjusted parameters for each electrode pair;

polling the corresponding adjusted parameters with the control and evaluation unit during a measuring mode for each connected electrode pair and for adjusting said measuring amplifier according to said adjusted parameters.

12. A method in accordance with claim 11, further comprising:
providing an analog control loop circuit with a differential amplifier having an input connected to the output of one of said common-mode signal electrodes and having another input connected to the output for the common-mode signal generated additionally;
connecting the output of said differential amplifier to another said common-mode signal electrodes, wherein the control and evaluating unit is set up to ground the output for the additional common-mode signal.

13. A method in accordance with claim 11, wherein said control and evaluating unit is set up to make available said additional common-mode signal with a same frequency as that of said symmetrical AC power source.

14. An electroimpedance tomograph in accordance with claim 11, further comprising:
providing compensating members with at least one ohmic resistor, with at least one capacitor and with at least one said transistor;
connecting said compensating members in one of the branches of said measuring amplifier to adjust said measuring amplifier;
driving said at least one transistor by said control and evaluating unit via digital-analog converters in order to make it possible to minimize a common-mode signal present at said measuring amplifier at the output of said measuring amplifier by adjusting according to value and phase.

15. An electroimpedance tomograph system in accordance with claim 14, wherein a first compensating member is coupled with the ground with said ohmic resistor and with said transistor and a second compensating member is coupled with the ground with said capacitor and with another transistor, wherein said transistors can be driven by said control and evaluating unit via said digital-analog converters.

* * * * *